(12) United States Patent
Hubbard et al.

(10) Patent No.: US 10,864,819 B2
(45) Date of Patent: Dec. 15, 2020

(54) DRIVER ALERTNESS WARNING SYSTEM AND METHOD

(71) Applicant: SPEEDGAUGE, INC., San Francisco, CA (US)

(72) Inventors: Jonathan Hubbard, San Francisco, CA (US); Christopher A. Kantarjiev, Palo Alto, CA (US)

(73) Assignee: SPEEDGAUGE, INC., San Francisco, CA (US)

( * ) Notice: Subject to any disclaimer, the term of this patent is extended or adjusted under 35 U.S.C. 154(b) by 0 days.

(21) Appl. No.: 16/177,338

(22) Filed: Oct. 31, 2018

(65) Prior Publication Data

US 2019/0126752 A1 May 2, 2019

Related U.S. Application Data

(60) Provisional application No. 62/579,708, filed on Oct. 31, 2017.

(51) Int. Cl.

| *B60Q 1/00* | (2006.01) |
| *B60K 28/06* | (2006.01) |
| *A61B 5/18* | (2006.01) |
| *B60W 40/09* | (2012.01) |
| *G08B 21/04* | (2006.01) |
| *G08B 21/06* | (2006.01) |
| *B60W 40/08* | (2012.01) |
| *B60K 31/00* | (2006.01) |

(52) U.S. Cl.
CPC ............ *B60K 28/066* (2013.01); *A61B 5/18* (2013.01); *B60W 40/09* (2013.01); *G08B 21/0407* (2013.01); *G08B 21/06* (2013.01); *B60K 31/0066* (2013.01); *B60T 2201/086* (2013.01); *B60W 2040/0818* (2013.01)

(58) Field of Classification Search
CPC .... A61B 5/18; B60K 28/066; B60K 31/0066; B60T 2201/086; B60W 2040/0818; B60W 40/09; G08B 21/0407; G08B 21/06
USPC ......................................................... 340/438
See application file for complete search history.

(56) References Cited

U.S. PATENT DOCUMENTS

| 2009/0021356 | A1* | 1/2009 | Galley | G08B 21/06 340/425.5 |
| 2010/0102972 | A1* | 4/2010 | Middlekauff | G08B 21/06 340/576 |
| 2015/0092056 | A1* | 4/2015 | Rau | B60R 1/02 348/148 |
| 2017/0349186 | A1* | 12/2017 | Miller | B60W 40/08 |
| 2018/0299890 | A1* | 10/2018 | Ewert | B60W 50/14 |

* cited by examiner

*Primary Examiner* — Naomi J Small
(74) *Attorney, Agent, or Firm* — Polsinelli LLP

(57) ABSTRACT

The present disclosure is directed to systems and methods avoiding collisions by monitoring the presence and alertness of a person in a vehicle. The alertness of that person may be monitored by identifying actions performed by that person when an automated driving assistant is used in a vehicle. Systems and method consistent with the present disclosure may monitor the alertness of a person that is located in a driving position of a vehicle according to criteria associated with particular individuals or with criteria associated with specific protocols. When a system or method consistent with the present disclosure identifies that a person is not alert, a corrective action may be initiated that reduces likelihood of a collision.

22 Claims, 6 Drawing Sheets

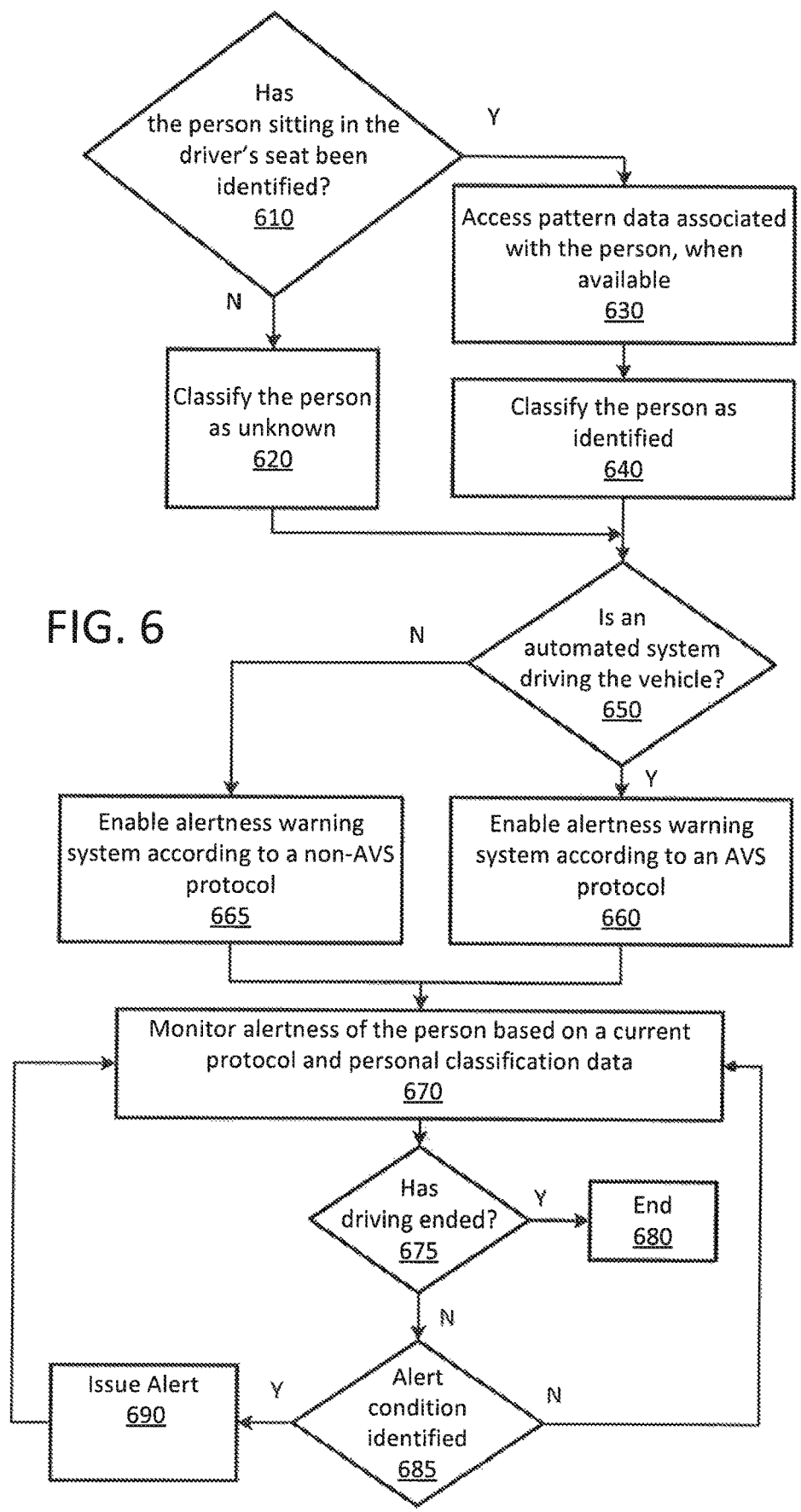

DRIVER ALERTNESS WARNING SYSTEM AND METHOD

CROSS-REFERENCE TO RELATED APPLICATIONS

The present application claims the priority benefit of U.S. provisional patent application No. 62/579,708 filed Oct. 31, 2017, the disclosure of which is incorporated herein by reference.

BACKGROUND OF THE INVENTION

Field of the Invention

The present invention is generally directed to systems and methods for monitoring the alertness of a person in a vehicle. More specifically, the present invention concerns monitoring driver behavior and detecting when the driver becomes inattentive so as to trigger a warning.

Description of the Related Art

Presently, the number of vehicles that are driven on the road using some form of automated driving assistant is increasing every day. Automated driving assistants—such as cruise control systems, collision avoidance systems, speed limiter systems, and lane departure systems—are increasing every day. Such systems may be implemented using an electronic control system or a computer that monitors information sensed by one or more sensors to accomplish a goal of helping a driver drive more safely.

Cruise control systems may use a sensor coupled to a comparator or to a computer that compares a speed set by a driver to the current speed of a vehicle. Speed limiting systems may limit the speed of a vehicle to a maximum speed or to a speed that is associated with a speed limit of a specific roadway where that vehicle is currently traveling.

Vehicle speed limiting systems may also receive speed limit information via wireless communications from a data center based on the GPS positon of the vehicle at a particular moment in time. These wireless communications can provide the computer of a vehicle with speed limit information in real-time as a vehicle is driven down a specific roadway. Typically, this speed limit information is used to limit the maximum speed that the computer will drive the vehicle down that specific roadway. Such systems may have no capability of identifying that a driver is alert and is able to respond to events that may cause an accident.

Collision avoidance systems may use a camera or radar coupled to a computer in a vehicle to identify the position of that vehicle relative to other vehicles on the roadway as that vehicle travels down a roadway. Such a computer may receive a data stream of information from the camera or radar from which the computer may make determinations relating to whether a vehicle is approaching another vehicle too quickly after which the computer may cause the braking system of a vehicle to slow or stop the vehicle, preventing it from hitting the other vehicle. In another instance, collision avoidance systems may warn a driver when another vehicle is in a blind spot in an attempt to tell the driver not to change lanes when that other vehicle is in the blind spot.

Lane departure systems may use a camera coupled to a computer that identifies the position of a vehicle relative to lines on a roadway, when the computer detects that the vehicle appears to be about to move out of a particular lane on the road, the computer may provide an alert to the driver of the vehicle to help prevent that driver from allowing the vehicle to depart a lane inadvertently.

Drivers that have become used to the function of an automated driving assistant may become over-reliant on those systems. For example, a driver using cruise control or speed limiter may rely on those systems to control the speed of a vehicle even as that vehicle rapidly approaches another vehicle from behind. If that driver is not attentive to the roadway at that moment, the vehicle may collide with that other vehicle.

A driver that is over-reliant on a collision avoidance system may assume that such a system will automatically prevent them from being involved in a collision from any direction, causing that driver to be inattentive. For example, a driver may be unaware that his collision avoidance system is not designed to identify that a vehicle approaching from the side presents a collision threat to his or her vehicle. In such an instance, an inattentive driver may not notice a vehicle approaching their vehicle from the side, and a collision may happen that otherwise could have been avoided.

Imperfections in a lane departure system may also cause a vehicle to move out of a lane inappropriately, thereby raising the risk of collision. This may occur when a roadway does not have perfect lines that cause that system to misidentify where the lane really is. For example, a roadway under constructions may have more than one set of lines marking a lane. Further, lines on a roadway may be obscured by the presence of water or snow.

Such prior art systems generally focus on the external environment or the vehicle itself rather than the driver. One way to mitigate the potential for a flaw or fault that may cause an autonomous vehicle to crash is for the driver of the vehicle watching or being aware of what their vehicle is doing and for that person to be ready to take over control (from an automated driving assistant or the autonomous vehicle itself) when they believe that system is not identifying a threat that may cause the vehicle to crash, otherwise collide with an obstacle, cause injury, or other undesired result. While drivers that use an automated driving assistant may know that they have the ability to take over driving control of the vehicle, such knowledge in itself does not guarantee that a driver of such a vehicle is actually watching the roadway for threats. Moreover, the availability of such systems may actually cause the driver to pay less attention. As such, a driver that relies too much on an automated driving assistant may be at greater risk of being involved in an accident as compared to other drivers that are more attentive to the roadway.

It may be quite complex and difficult to analyze driver behavior, however, as different drivers may display different signs of inattentiveness or other behaviors that increase the likelihood of vehicle collision. Further, the same behavioral indicators may signify inattentiveness in one driver, but may not in other drivers. The driver themselves may not be aware of what behavioral indicators are signs of inattentiveness, thereby making the process of identifying such indicators more difficult. Moreover, such behavioral signs may further span visual, audio, biometric, and other behaviors that may be detectable. Further, a driver may exhibit different combinations of the same indicators, but the different combinations may indicate different things in different contexts.

What are needed are systems and methods that identify that a driver is not attentive to the roadway such that the risk of accidents caused by inattentive drivers may be reduced.

SUMMARY OF THE PRESENTLY CLAIMED INVENTION

The presently claimed invention relates to a system, a method, and a non-transitory computer-readable storage medium for monitoring whether a person in a driving positon of a vehicle is alert. A method consistent with the present disclosure may receive sensor data from one or more sensors at a vehicle when an automated driving assistant at the vehicle is operational, next an analysis using the received sensor data may be performed, and then an identification that the person is not alert may be made based on the analysis. After the person is identified as not being alert, a corrective action may be performed.

Similarly when the presently claimed invention may be implemented as a non-transitory computer readable medium including program code executable by a processor, the method may include receiving sensor data from one or more sensors at a vehicle when an automated driving assistant at the vehicle is operational, then an analysis using the received sensor data may be performed, and an identification that a person in a driving positon the vehicle is not alert may be made based on the analysis. After the person is identified as not being alert, a corrective action may be performed.

A system consistent with the present disclosure may include one or more sensors, a memory, and a processor, where the processor executes instructions out of the memory to receive sensor data from the sensors, perform analysis on the received sensor data, identify that a person in a driving position of a vehicle is not alert, and initiate a corrective action based on the identification that the person is not alert.

BRIEF DESCRIPTION OF THE DRAWINGS

FIG. 2 illustrates an exemplary lane of a roadway that a vehicle may be driving on.

FIG. 6 illustrates a series of steps that may be performed by methods and apparatus consistent with the present disclosure.

DETAILED DESCRIPTION

Figure 1:
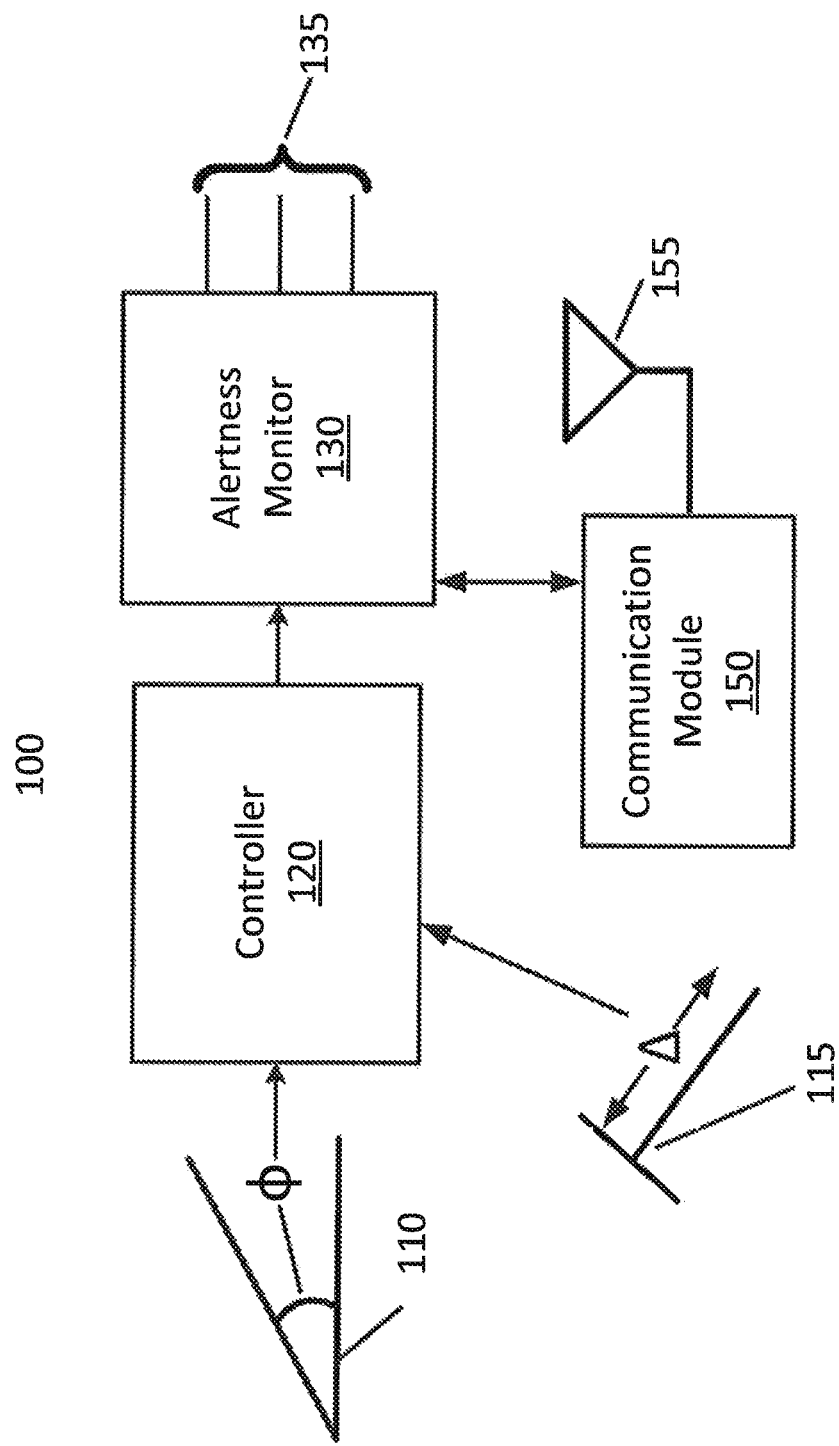
FIG. 1 illustrates an exemplary sub-system that may be implemented in a vehicle for monitoring the alertness of a person in a driving position of the vehicle.

The present disclosure is directed to systems and methods avoiding collisions by monitoring the presence and alertness of a driver of a vehicle. The alertness of that driver may be monitored by identifying actions performed by that driver when an automated driving assistant is used in a vehicle. When a system or method consistent with the present disclosure identifies that a driver is not alert, a corrective action may be initiated that reduces likelihood of a collision.

By scanning for information regarding driver behavior, a behavior profile may be constructed. The driver profile may communicate granular information about patterns of potentially risky behaviors produced by the behavior-based scan (e.g., by various sensors in the vehicle). Such driver behavior profiles may therefore be used to detect when a specific driver in a vehicle is exhibiting behavior that elevates the risk of adverse results. The use of such driver behavior profile further provides for flexible and nuanced behavioral analysis related to driving risks. Once a driver profile is constructed, the system can review such profile data in order to further construct rules by which to identify which behaviors represent risk in a specific driver, car, and driving context.

Corrective actions consistent with the present disclosure may then be taken, including providing an alert to a driver of a vehicle or may include sending a message to their home office/boss that indicates that the driver appears not to be alert enough to override an automated driving assistant if required. Corrective actions may also include sending communications to the driver indicating that they should pay more attention to the roadway when an autonomous system is driving a vehicle.

Systems and methods consistent with the present disclosure may identify that a driver is alert based on that driver occasionally overriding an automated driving assistant. In instances where the person does not override a driving assistant for a period of time, the system could identify that that person is not attentive. For example, when cruise control is used, a system consistent with the present disclosure may identify that the driver should occasionally tap the brakes to slow down or may occasionally press on the accelerator during the course of normal driving when the cruise control is operational. Here, the system could detect the person tapping the brakes as the vehicle approaches another vehicle, for example. This could be accomplished by a sensor (coupled to a processor) that senses the person pressing on the brake.

A person driving in a vehicle that uses an automated speed limiting system may be inclined to press on the gas pedal or brakes in instances when that person wants to drive faster or has to drive slower. Systems and methods consistent with the present disclosure may adapt or learn the behavior of a particular driver when identifying patterns of that driver that may be used as a baseline for setting one or more parameters that may be used to identify the attentiveness of that particular driver. For example, sensors sensing the location of a vehicle's steering wheel may be used to identify that the driver is maintaining a location within a lane by changing the location of the vehicle's steering wheel every three seconds. Based on this, a system that monitors the alertness of a driver may identify that the driver is not alert when that driver has not moved the steering wheel in the last three seconds.

Systems and methods consistent with the present disclosure may also monitor a variance from a lane center position in a lane of a roadway. When such a system detects that a driver is allowing their vehicle to stray back and forth from that lane center position to a greater degree over the course of a few seconds, an alert may be sent to the driver warning that driver to focus on driving.

Systems and methods consistent with the present disclosure may also rely on limitations inherent in in an automated driving assistant to identify that a driver is not alert. For example, in an instance where a speed limiting system is programmed to cause a vehicle to drive below a speed limit, an alertness monitoring system may expect the driver to press the accelerator occasionally. In an instance where such a driver does not press the accelerator for a period of time, a corrective action may be initiated by the alertness monitoring system.

In another instance a camera observing a person seated in the driver's seat of an vehicle using an automated driving assistant may stream data to a computer that performs an analysis of actions performed by that person. The analysis performed by the computer may include identifying whether the person in the driver's seat is looking at where the vehicle is driving. For example, by identifying that that person is looking forward through the windshield of the vehicle. The analysis may also identify whether the person is not looking in an appropriate direction for a span of time greater than a threshold amount of time. In other instances, an alertness monitoring system may identify that a driver is engaged in a behavior that may be dangerous, such as texting while driving or closing their eyelids for greater than a threshold time limit. A determination could be made by processor analyzing facial data that identifies whether the person in the driver's seat is looking forward or not, or identify whether that person has closed their eyes too long.

In yet other instances, the driver of a vehicle may need to provide a response according to a rule. For example, the rule may dictate that a driver salute, raise their hand, say a word, push a button, or perform another action when they approach a signal light. Similarly, the driver may be expected to provide a response when a light on their dashboard turns on or when otherwise prompted by another visual or audio que. In such instances visual or audio ques may be in response to something that the vehicle approaches or passes or may be in response to an audio or visual que provided by an accident avoidance system consistent with the present disclosure. A camera, computer, or other sensor may identify that the person has provided a correct response according to the rule.

Furthermore, apparatus and methods consistent with the present disclosure may be coupled to a heads up display that projects images on to the windshield of the vehicle. A computer coupled to a camera or other sensor may then identify how the person seated in a driver's seat reacts to visual data presented on the vehicle's windshield.

As such, a system that monitors actions of a driver may identify patterns performed by that individual driver when an automated driving assistant is used.

FIG. 1 illustrates an exemplary sub-system that may be implemented in a vehicle for monitoring the alertness of a person in a driving seat of the vehicle. The sub-system 100 of FIG. 1 includes a vehicle accelerator (i.e. a throttle or gas pedal) 110, a brake pedal 115, a controller 120, an alertness monitor 130, and a communication module 150. When a driver depresses accelerator 110, a measure relating to how much the accelerator is depressed may be sensed by controller 120. The measure of accelerator depression may correspond to an angle like $\phi$ of FIG. 1. As such, $\phi$ may correspond to a measure of resistance when accelerator 110 is coupled to a rheostat (not depicted). Similarly, a measure relating to how much brake pedal 225 is depressed may be sensed by controller 120 when the driver depresses brake pedal 115 by an amount that corresponds to a difference measure of delta $\Delta$, for example.

Communication module may be used to send communications to a driver's boss in the advent that alertness monitor 130 identifies that a drive is not alert. Communication module 150 may be implemented via any type of communication technology, including yet not limited to wireless cellular (2G, 3G, 4G, or other) communications, radio communications, or other communication technology standard in the art. Alternatively or additionally alertness monitor 130 may issue an alert to the driver via outputs 135. Outputs 135 may provide an audio or visual alert to the driver that warns the driver that they appear to be inattentive.

While not illustrated in FIG. 1, the a vehicle associated with the alertness monitoring system of FIG. 1 may also include a global positioning system (GPS) that identifies a GPS location of that vehicle as it drives down a roadway. In such an instance, communications used to control the maximum speed of the vehicle may be received via communication module 150 or another communication module periodically that set a maximum speed that a vehicle should not exceed at a particular location. In such an instance a driver pressing on accelerator 110 or brake 115 may be received by controller 120 and controller 120 may communicate changes in accelerator position $\phi$ or brake pedal position $\Delta$ to alertness monitor 130 as the alertness of the driver is monitored. In this instance, controller 120 may also be used to limit the maximum automated speed of the vehicle when the driver is not currently depressing the brake pedal 115 or the accelerator 110, for example. While the maximum speed of a vehicle may be limited by controller 120, the present disclosure is not limited to this technique, however. Alternatively, an automated driving assistant and an alertness monitoring system may be independent systems.

Figure 2:
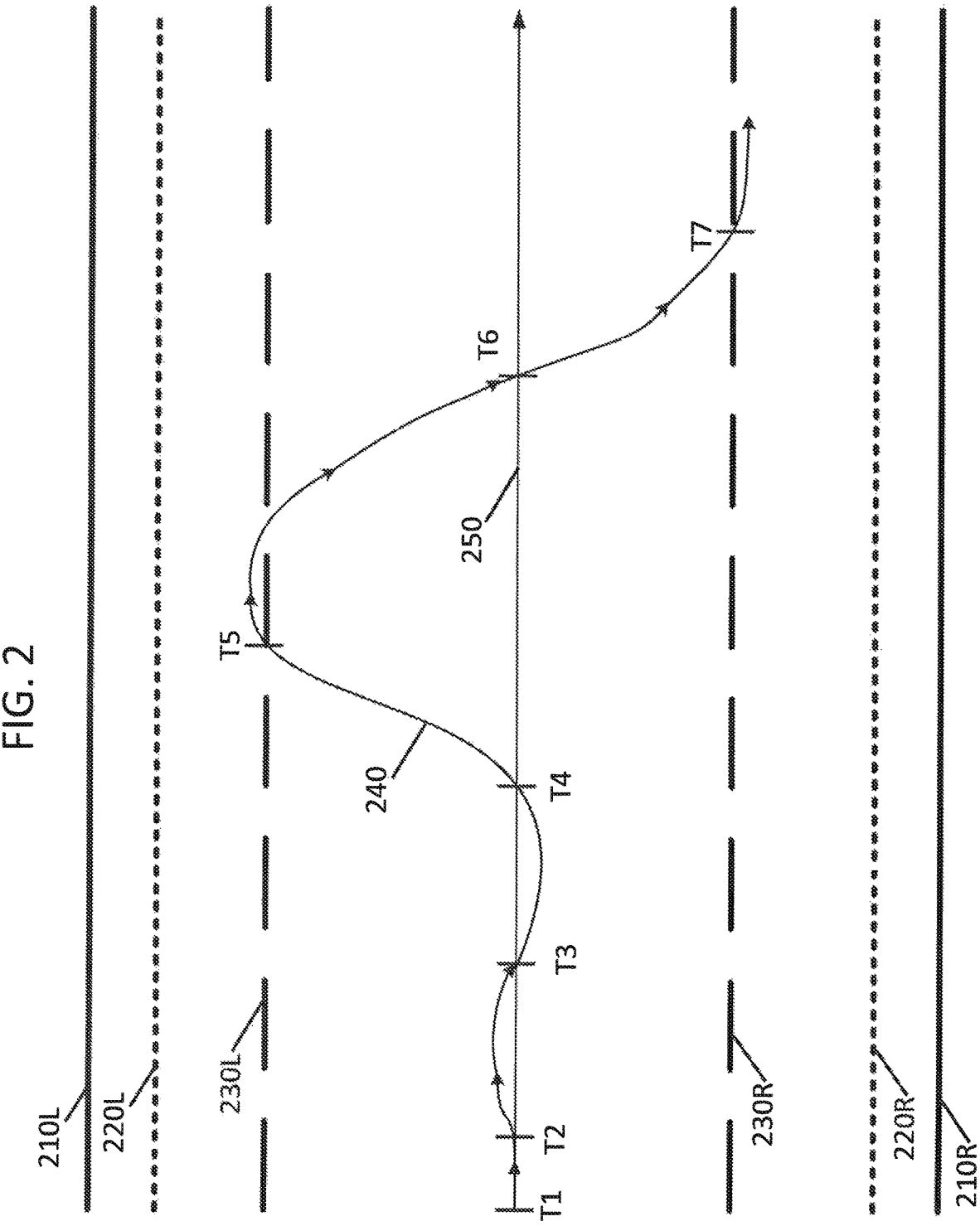

FIG. 2 illustrates an exemplary lane of a roadway that a vehicle may be driving on. FIG. 2 includes lane lines 210L and 210R, departing lane limits 220L and 220R, lane variance threshold lines 230L and 230R, path of travel line 240, and an imaginary lane center line 250 of a roadway lane. Points T1, T2, T3, T4, T5 and T6 illustrates points that follow the path of travel line 240 over time. The path of travel line 240 may generally identify the path that a particular vehicle traveled along the roadway.

Note that at points T2, T3, T4 and T6 that the vehicle crossed the center 250 of the lane. Between points T1 and T2 the vehicle traveling along the roadway stayed very close to the center line 250. Note also that between points T2 and T3 that the vehicle traveled slightly to the left of the center line 250 and the between points T3 and T4 traveled slightly to the right of center line 250. After point T4 the vehicle veers to the left and at point T5 at least a portion of the vehicle crosses lane variance threshold line 230L and then after point T5 the vehicle begins veering to the right. The vehicle then crosses the center line 250 at point T6 and crosses the lane variance line 230R at point T7.

In an instance where a portion of a vehicle crosses lane departure line 220L or 220R, a departure system may identify that that vehicle is about to cross line 210L or 210R and cross into another lane of the roadway. In certain instances, lane variance threshold lines 230L and 230R may be used by systems consistent with the present disclosure to monitor how variable a driver drives down a lane of a roadway. Note that in FIG. 2 that lane variance lines 230L and 230R are not as close to lane lines 210L and 210R as lane departure lines 220L and 220R.

FIG. 2, thus, illustrates that a vehicle traveling down a roadway never truly stays in the center 250 of the lane, instead vehicles tend to be driven back and forth relative to the center line 250 of a lane in a road. Because of this, the path that a driver drives a vehicle down a roadway may be associated with a variance distance (amplitude) and a periodicity, where the variance may be related to how far from the center line a vehicle moves over time and where the periodicity may be related to how frequently a driver make corrections to keep the vehicle in the center of a lane of a road. Such a periodicity may be referred to as a stray period that may be related to how frequently a vehicle strays from a first relative position on a roadway to another relative position on the roadway and then back to the first relative position of the roadway. The variance and periodicity of a vehicle may, thus, be similar to the amplitude and period of a sine wave that may change over time.

An attentive driver may be associated with a driving pattern that has a low variance or with a driving pattern that has both a low variance and a low periodicity. As such, an attentive driver will tend not to drive their vehicle very far off of a road lane's imaginary center line and an attentive driver may not perform many directional changes while keeping their vehicle in the center of a lane.

The identification that a variance associated with a particular driver has increased may be used to identify that that particular driver not alert. When a variance associated with a driver increases beyond or reaches a threshold amount, a determination may be made by systems consistent with the present disclosure that the driver of that vehicle is not attentive/alert. As such, when the a driver allows a portion of their vehicle to stray beyond lane variance line 230L at point T5 a warning may be sent to the driver indicating that they should be more attentive.

Alternatively, a warning may only be sent to the driver when a vehicle has crossed a lane variance line more than once in a given period set or in a given time frame. Hence, a warning may not be sent to the driver at point T5, instead a warning may be sent a point T7 because the driver crossed at least one of the lane variance lines 230L or 230R twice over a given time or stray period.

Methods and systems of the present disclosure may also work with a collision avoidance system by identifying that a driver acts before a collision avoidance system would typically cause a braking function to be initiated. Such methods and systems may also issue a warning to the driver before a collision avoidance system is anticipated to be initiated by identifying that a driver has allowed their vehicle to approach within a threshold distance of another vehicle. As such, a warning may be issued by an alertness monitoring system before a collision avoidance system causes the vehicles brakes to be applied. In such instances, a single system may implement both an alertness monitoring function and a collision avoidance function or these functions may be performed by different systems with different constraints or rules.

Alternatively or additionally, a variance may be related to how quickly the vehicle moves from one position in a lane to another position in that lane. A more jerky response input by a driver may indicate that the driver is not alert.

Figure 3:
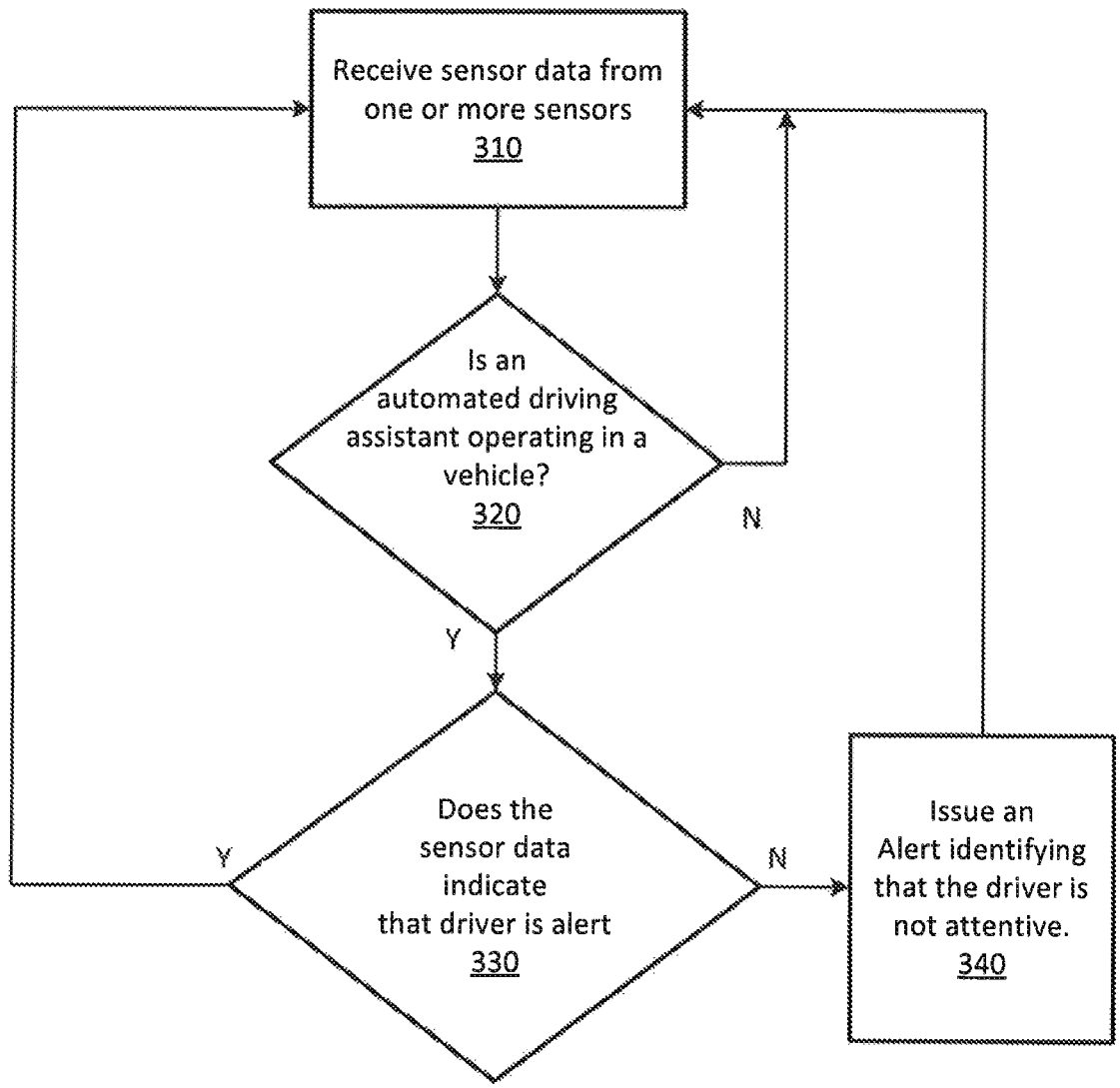
FIG. 3 illustrates an exemplary method consistent with the present disclosure.

FIG. 3 illustrates an exemplary method consistent with the present disclosure. Step 310 of the flow chart of FIG. 3 is where sensor data from one or more sensors in an autonomous vehicle are provided to a computer monitors a driver of a vehicle. Here again sensor data may sense when the driver brakes, when the driver presses the accelerator, or when and how much the driver steers the vehicle. This sensor data may also be streaming data from a camera that may be used to identify whether a driver is watching the road, is closing their eyes, is texting, or is driving with a high level of variability.

Next in determination step 320, the computer may identify whether an automated driving assistant is operating in a vehicle, when no program flow may flow back to step 310 where additional sensor data is received. Alternatively program flow may end when the automated driving assistant is not operating or program flow may perform actions relating to monitoring the driver's alertness even when an automated driving assistant is not operational or present in the vehicle.

When step 320 identifies that an automated driving assistant is operating in a vehicle, program flow moves to determination step 330 that may identify that the driver is alert. This may be performed by monitoring actions regarding the driving of the vehicle or by monitoring whether the driver affects a function associated with the automated driving assistant. When determination step 330 identifies that the driver is alert program flow moves back to step 310 where more sensor data is received. When determination step identifies that the driver is not alert, program flow moves to step 340 that issues an alert that identifies that the driver is not attentive (not alert). After step 340 program flow moves back to step 310 where more sensor data is received.

Figure 4:
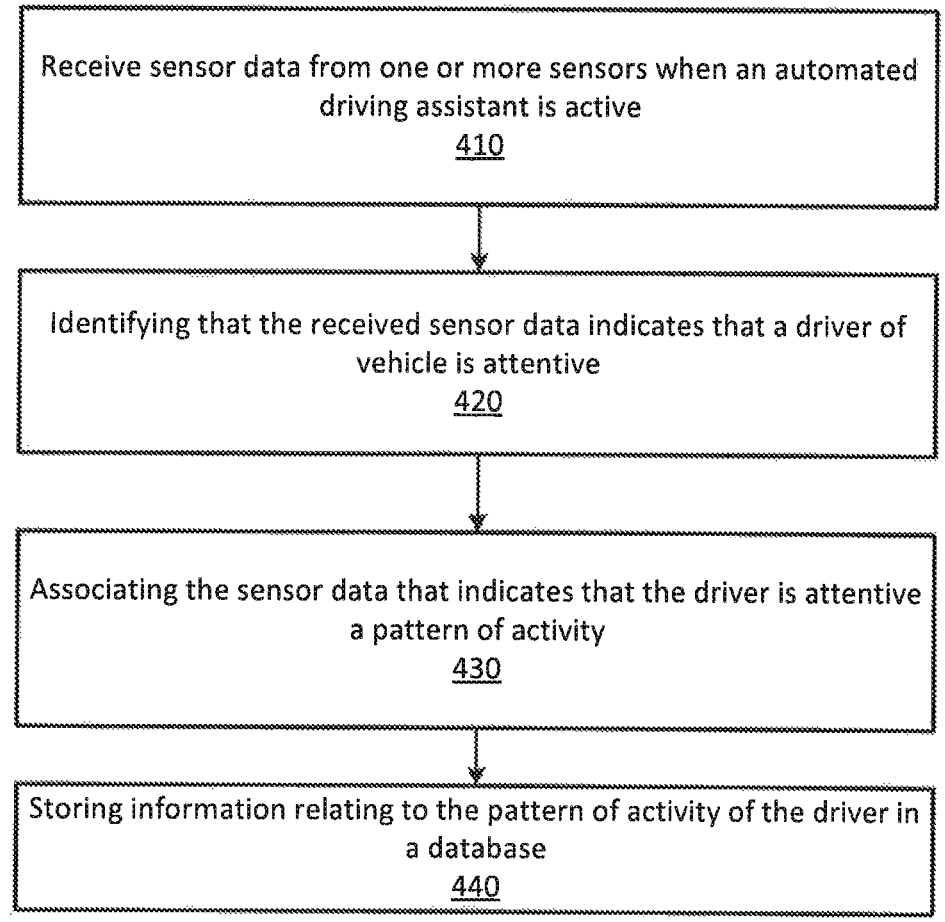
FIG. 4 illustrates a second exemplary method consistent with the present disclosure.

FIG. 4 illustrates a second exemplary method consistent with the present disclosure. Step 410 of FIG. 4 is a step where a computer may receive sensor data from sensors in a vehicle when an automated driving assistant is active (operational). Although not illustrated in FIG. 4, the identity of driver may be identified before the sensor data is received in step 410. Next step 420 identifies that the received sensor data appears to indicate that a drive of the vehicle is attentive. After step 420 the received sensor data that indicates that the person is attentive may be associated with a pattern of activity of the driver. Finally in step 440 information relating to the pattern of activity of the person may be stored in a database.

The information stored in the database in step 440 of FIG. 4 may be unique to a particular person. This is because, in a given a set of circumstances one person may react to a type of even in a manner different than another person. For example, a first person may prefer to maintain a larger following distance than a second person when their vehicle is following another vehicle. In another example, one person may wish to drive as fast as possible where another person may always wish to drive slower than the speed limit. In yet another instance a given driver may drive with a greater variance or periodicity relative to an imaginary center line of a lane of a roadway. When the same person drives in the autonomous vehicle again, their pattern of activity may be used to identify that the driver is attentive with a greater degree of accuracy. As such, systems and methods consistent with the present disclosure may improve continuously over time. Furthermore, historical driver pattern data may be compared with current data sensed at the vehicle to identify that an identified person is not alert.

Figure 5:
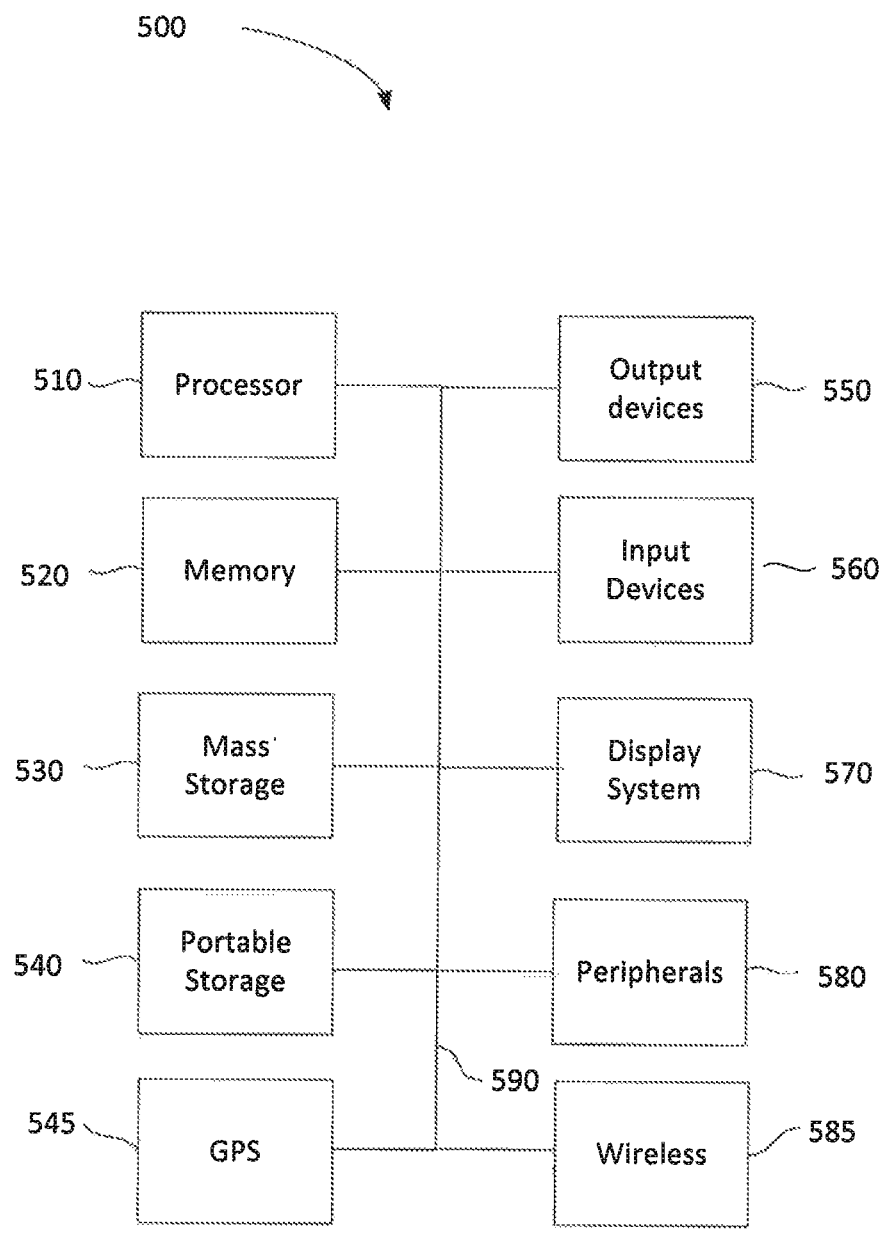
FIG. 5 illustrates an exemplary computing system that may be used to implement all or a portion of a device for use with the present technology.

FIG. 5 illustrates an exemplary computing system that may be used to implement all or a portion of a device for use with the present technology. The computing system 500 of FIG. 5 includes one or more processors 510 and memory 520. Main memory 520 stores, in part, instructions and data for execution by processor 510.

Main memory 520 can store the executable code when in operation. The system 500 of FIG. 5 further includes a mass storage device 530, portable storage medium drive(s) 540, a GPS system 545, output devices 550, user input devices 560, a graphics display 570, peripheral devices 580, and a wireless communication system 585. The components shown in FIG. 5 are depicted as being connected via a single bus 590. However, the components may be connected through one or more data transport means. For example, processor unit 510 and main memory 520 may be connected via a local microprocessor bus, and the mass storage device 530, peripheral device(s) 580, portable storage device 540, and display system 570 may be connected via one or more input/output (I/O) buses. Mass storage device 530, which may be implemented with a magnetic disk drive, solid state drives, an optical disk drive or other devices, may be a non-volatile storage device for storing data and instructions for use by processor unit 510. Mass storage device 530 can store the system software for implementing embodiments of the present invention for purposes of loading that software into main memory 520.

Portable storage device 540 operates in conjunction with a portable non-volatile storage medium, such as a FLASH thumb drive, compact disk or Digital video disc, to input and output data and code to and from the computer system 500 of FIG. 4. The system software for implementing embodiments of the present invention may be stored on such a portable medium and input to the computer system 500 via the portable storage device 540.

Input devices 560 provide a portion of a user interface. Input devices 560 may include an alpha-numeric keypad, such as a keyboard, for inputting alpha-numeric and other information, or a pointing device, such as a mouse, a trackball, stylus, or cursor direction keys. Additionally, the system 500 as shown in FIG. 5 includes output devices 550. Examples of suitable output devices include speakers, printers, network interfaces, and monitors.

Display system 570 may include a liquid crystal display (LCD) or other suitable display device. Display system 570 receives textual and graphical information, and processes the information for output to the display device.

Peripherals 580 may include any type of computer support device to add additional functionality to the computer system. For example, peripheral device(s) 580 may include a modem or a router.

GPS system 545 may include an antenna (not illustrated in FIG. 5) that receives global positioning information from one or more satellites such that a location associated with a current location of computer system 500 may be identified and provided to processor 510 via bus 590.

FIG. 5 also includes a wireless communication system 585 that may include an antenna (not illustrated in FIG. 5). Wireless communication system 585 may be configured to receive or transmit information via any standard wireless communication technology standard in the art. As such, wireless communication system 585 may receive or transmit information according to a wireless (2G, 3G, 4G, blue-tooth, 802.11, light strobes, or other) cellular or device to device standard, or may use radio or optical communication technologies. Wireless communication system may be configured to receive signals directly from pieces of infrastructure along a roadway (such as a signal light or roadway sensors), may be configured to receive signals associated with an emergency band, or may be configured to receive beacons that may be located at a service or emergency vehicle. Computer systems of the present disclosure may also include multiple wireless communication systems like communication system 585.

The components contained in the computer system 500 of FIG. 5 are those typically found in computer systems that may be suitable for use with embodiments of the present invention and are intended to represent a broad category of such computer components that are well known in the art. Thus, the computer system 500 of FIG. 5 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Android, and other suitable operating systems.

FIG. 6 illustrates a series of steps that may be performed by methods and apparatus consistent with the present disclosure. FIG. 6 includes determination step 610 that identifies whether a person sitting in the driver's seat of a vehicle has been identified, when no, program flow moves from step 610 to step 620 of FIG. 6 where the person in the driver's seat is classified as unknown. Personal identification may be performed using fact recognition software, may be identified by user input, or may be identified using personal biometric information. When determination step 610 identifies that the person in the driver's seat is known, program flow moves to step 630 where access pattern data associated with that identified person may be accessed (when such data is available). Step 640 of FIG. 6 may classify the person as being identified and may also use stored pattern data as part of that person's classification. Classification data may be used to set parametrics associated with an alertness monitoring system based on a set of operating characteristics.

After a personal classification has been made in either step 620 or step 640 of FIG. 6, program flow may move to determination step 650 that identifies whether an automated system is currently driving the vehicle, when yes, program flow may move to step 660 where an alertness warning system may be enabled to operate according to criteria associated with an automated vehicle system (AVS) protocol. When an automated system is not driving the vehicle, program flow may move from step 650 to step 665 where an alertness warning system may be enabled to operate according to a criteria associated with a non-AVS protocol. AVS protocol criteria may differ from non-AVS protocol criteria.

After either step 660 or 665, program flow may move to step 670 where the alertness of the person in the driving seat may be monitored based on a current protocol. In certain instances characteristics of a current protocol may be based on personal classification information/data (e.g. driving history, age, or skill level). In an instance where the automated system is currently driving the vehicle, an AVS protocol may rely more on watching a person's eyes and head motions more than watching how or when that person adjusts how the vehicle is being driven by the automated system. In instances when an automated system is currently not driving the vehicle, a non-AVS protocol may rely on watching what actions the driver performs as the vehicle moves down a roadway and rely on watching the eyes of a person when identifying a measure of driver alertness. A non-AVS protocol may be more concerned with monitoring the periodicity or variance how far from the center line a vehicle moves over time than an AVS protocol would be, for example. As such, the functionality of an alertness monitor may be optimized to track actions of a person based on criteria associated with different protocols or different driver classifications.

After step 670, determination step 675 may identify whether driving has ended, when yes program flow may move to step 680, where program flow ends. When driving has not ended, program flow may move to determination step 685 that identifies whether an alert condition has been identified, when no program flow moves to step 690, where an alert is issued. When step 685 identifies that an alert condition has not been identified or after step 690, program flow may move back to step 670 where the alertness monitoring of the person is continued.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

What is claimed is:

1. A method for monitoring driver behavior, the method comprising:
storing one or more driver profiles in memory, wherein each driver profile specifies a set of behavioral risk factors specific to each different driver;
receiving sensor data from one or more sensors in a vehicle when an automated driving assistant is operating, wherein at least part of the sensor data concerns one or more inputs to one or more vehicle controls of the vehicle by a current driver in the vehicle that adjust positioning of the vehicle in a roadway lane to correct one or more variations of the vehicle from a center of the roadway lane;
retrieving a driver profile specific to the current driver;
identifying that a periodicity of the one or more variations from the center of the roadway lane corresponds to the one or more inputs to the one or more vehicle controls that adjust the positioning of the vehicle in the roadway lane;
analyzing the received sensor data to identify that the current driver of the vehicle is exhibiting risky behavior based on the periodicity exceeding a periodicity threshold associated with the driver profile; and
performing a corrective action based on the identification that the current driver of the vehicle is exhibiting the risky behavior.

2. The method of claim 1, further comprising identifying an identity of the current driver of the vehicle.

3. The method of claim 2, wherein the retrieved driver profile includes one or more patterns of activity associated with the current driver, and wherein analyzing the received sensor data includes comparing the sensor data to the one or more patterns in the retrieved driver profile.

4. The method of claim 1, further comprising:
classifying the current driver;
identifying that an automated driving system is driving the vehicle; and
enabling the automated driving assistant according to an automated vehicle system (AVS) protocol.

5. The method of claim 1, further comprising:
classifying the current driver;
identifying that an automated driving system is not driving the vehicle; and
enabling the automated driving assistant according to a non-automated vehicle system (non-AVS) protocol.

6. The method of claim 1, further comprising:
setting a monitoring mode of the automated driving assistant according to an automated vehicle system (AVS) protocol of a plurality of protocols, the plurality of protocols including the AVS protocol associated with a first criteria set and a non-AVS protocol associated with a second criteria set that differs from the first criteria set, the first criteria set associated with operation of the automated driving assistant according to the automated vehicle (AVS) protocol rather than the non-AVS protocol; and
monitoring behavior of the current driver according to the AVS protocol, wherein the identification that the current driver is exhibiting the risky behavior is also based on the AVS protocol setting and the first criteria set.

7. The method of claim 6, further comprising tracking one or more actions associated with the analyzed sensor data according to the AVS protocol and the first criteria set.

8. The method of claim 1, further comprising identifying a threshold level of vehicle variance associated with the one or more vehicle variations, the threshold level of vehicle variance identifiable by a period and an amplitude of a movement of the vehicle on the roadway when the automated driving assistant is disabled, wherein the analysis of the received sensor data also identifies that the current driver of the vehicle is exhibiting the risky behavior based on the period and the amplitude of the variance.

9. The method of claim 1, further comprising identifying that the current driver is exhibiting the risky behavior based on a timing of the one or more inputs.

10. A non-transitory computer-readable storage medium having embodied thereon a program executable by a processor for implementing a method for monitoring driver behavior, the method comprising:
storing one or more driver profiles in memory, wherein each driver profile specifies a set of behavioral risk factors specific to each different driver;
receiving sensor data from one or more sensors in a vehicle when an automated driving assistant is operating, wherein at least part of the sensor data concerns one or more inputs to one or more vehicle controls of the vehicle by a current driver in the vehicle that adjust positioning of the vehicle in a roadway lane to correct one or more variations of the vehicle from a center of the roadway lane;
retrieving a driver profile specific to the current driver;
identifying that a periodicity of the one or more variations from the center of the roadway lane corresponds to the one or more inputs to the one or more vehicle controls that adjust the positioning of the vehicle in the roadway lane;
analyzing the received sensor data to identify that the current driver of the vehicle is exhibiting risky behavior based on the periodicity exceeding a periodicity threshold associated with the driver profile; and
performing a corrective action based on the identification that the current driver of the vehicle is exhibiting the risky behavior.

11. The non-transitory computer-readable storage medium of claim 10, further comprising instructions executable to identify an identity of the current driver of the vehicle.

12. The non-transitory computer-readable storage medium of claim 10, wherein the retrieved driver profile includes one or more patterns of activity associated with the current driver, and wherein analyzing the received sensor data includes comparing the sensor data to the one or more patterns in the retrieved driver profile.

13. The non-transitory computer-readable storage medium of claim 10, further comprising instructions executable to:
classify the current driver;
identify that an automated driving system is driving the vehicle; and
enable the automated driving assistant according to an automated vehicle system (AVS) protocol.

14. The non-transitory computer-readable storage medium of claim 10, further comprising instructions executable to:
classify the current driver;
identify that an automated driving system is not driving the vehicle; and enable the automated driving assistant according to a non-automated vehicle system (non-AVS) protocol.

15. The non-transitory computer-readable storage medium of claim 10, further comprising instructions executable to:
set a monitoring mode of the automated driving assistant according to a first protocol of a plurality of protocols, the plurality of protocols including the first protocol associated with a first criteria set and a second protocol associated with criteria that differs from the first criteria set; and
monitor behavior of the current driver according to the first protocol, wherein the identification that the current driver is exhibiting the risky behavior is also based on the first protocol setting and the first criteria set.

16. The non-transitory computer-readable storage medium of claim 15, further comprising instructions executable to track one or more actions associated with the analyzed sensor data according to the first protocol and the first criteria set.

17. A system for monitoring driver behavior, the system comprising:
memory that stores one or more driver profiles, wherein each driver profile specifies a set of behavioral risk factors specific to each different driver;
one or more sensors that capture sensor data in a vehicle when an automated driving assistant is operating, wherein at least part of the sensor data concerns one or more inputs to one or more vehicle controls of the vehicle by a current driver in the vehicle that adjust positioning of the vehicle in a roadway lane to correct one or more variations of the vehicle from a center of the roadway lane; and
a processor that executes instructions stored in memory, wherein execution of the instructions by the processor:
retrieves a driver profile specific to the current driver;
identifies that a periodicity of the one or more variations from the center of the roadway lane corresponds to the one or more inputs to the one or more vehicle controls that adjust the positioning of the vehicle in the roadway lane;
analyzes the sensor data to identify that the current driver of the vehicle is exhibiting risky behavior based on the periodicity exceeding a periodicity threshold associated with the driver profile; and
performs a corrective action based on the identification that the current driver of the vehicle is exhibiting the risky behavior.

18. The system of claim 17, wherein the processor executes further instructions to identify an identity of the current driver of the vehicle.

19. The system of claim 18, wherein the retrieved driver profile includes one or more patterns of activity associated with the current driver, and wherein the processor analyzes the sensor data by comparing the sensor data to the one or more patterns in the retrieved driver profile.

20. The system of claim 17, wherein the processor executes further instructions to:
classify the current driver,
identify that an automated driving system is driving the vehicle, and
enable the automated driving assistant according to an automated vehicle system (AVS) protocol.

21. The system of claim 17, wherein the processor executes further instructions to:
classify the current driver,
identify that an automated driving system is not driving the vehicle, and
enable the automated driving assistant according to a non-automated vehicle system (non-AVS) protocol.

22. The system of claim 17, wherein the processor executes further instructions to:
set a monitoring mode of the automated driving assistant according to a first protocol of a plurality of protocols, the plurality of protocols including the first protocol associated with a first criteria set and a second protocol associated with criteria that differs from the first criteria set, and
monitor behavior of the current driver according to the first protocol, wherein the identification that the current driver is exhibiting the risky behavior is also based on the first protocol and the first criteria set.

* * * * *